US012788929B2

(12) United States Patent
Avasthi

(10) Patent No.: US 12,788,929 B2
(45) Date of Patent: Nov. 10, 2026

(54) AIR QUALITY ANALYSIS DEVICE

(71) Applicant: HONEYWELL INTERNATIONAL INC., Charlotte, NC (US)

(72) Inventor: Rahul Avasthi, Allen, TX (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 687 days.

(21) Appl. No.: 18/194,918

(22) Filed: Apr. 3, 2023

(65) Prior Publication Data

US 2024/0325671 A1 Oct. 3, 2024

(51) Int. Cl.
*G01N 33/00* (2006.01)
*A61M 16/10* (2006.01)

(52) U.S. Cl.
CPC ..... *A61M 16/1005* (2014.02); *G01N 33/0031* (2013.01); *A61M 2016/102* (2013.01)

(58) Field of Classification Search
CPC .......... G01N 33/0031; A61M 16/1005; A61M 2016/102
USPC .......................................................... 73/23.2
See application file for complete search history.

(56) References Cited

U.S. PATENT DOCUMENTS 5,503,146 A 4/1996 Froehlich et al.
5,551,419 A 9/1996 Froehlich et al.
6,085,576 A 7/2000 Sunshine et al.
6,266,995 B1 * 7/2001 Scott .................... G01N 33/007 422/94
7,165,547 B2 1/2007 Truitt et al.
9,615,773 B1 * 4/2017 Kayyali .................. A61B 5/08
9,839,726 B2 12/2017 Ehlert
10,695,516 B2 6/2020 Chaturvedi et al.
10,967,207 B2 4/2021 Son et al.
11,045,800 B1 6/2021 Kaplan et al.
12,203,668 B2 1/2025 Avasthi
(Continued)

FOREIGN PATENT DOCUMENTS

AU 2011356176 A1 7/2013
CA 2163855 A1 6/1996
(Continued)

OTHER PUBLICATIONS

Extended European Search Report Mailed on Apr. 9, 2024 for EP Application No. 23203471, 17 page(s).
(Continued)

*Primary Examiner* — Peter J Macchiarolo
*Assistant Examiner* — Rodney T Frank
(74) *Attorney, Agent, or Firm* — ALSTON & BIRD LLP

(57) ABSTRACT

An example air quality analysis device and a method of performing air quality analysis are provided herein. In some embodiments, the air quality analysis device has a housing having a chamber comprising an inlet port. In some embodiments, the inlet port is structured to receive an air flow into the chamber. In some embodiments, the air quality analysis device may include a plurality of sensors disposed within the chamber and configured to generate air quality data associated with the air flow. In some embodiments, the plurality of sensors comprises at least one mold sensor. In some embodiments, the air quality analysis device may include a printed circuit board in communication with the plurality of sensors and configured to transmit the air quality data to a computing device.

18 Claims, 7 Drawing Sheets

(56) References Cited

U.S. PATENT DOCUMENTS

| | | | | |
|---|---|---|---|---|
| 2007/0068530 | A1 | 3/2007 | Pacey | |
| 2008/0066741 | A1 | 3/2008 | Lemahieu et al. | |
| 2009/0020120 | A1 | 1/2009 | Schatzl et al. | |
| 2010/0036272 | A1 | 2/2010 | Mace et al. | |
| 2015/0283351 | A1 | 10/2015 | Castello et al. | |
| 2017/0246486 | A1 | 8/2017 | Cazier et al. | |
| 2017/0266399 | A1 | 9/2017 | Campana et al. | |
| 2018/0078723 | A1 | 3/2018 | Caruso et al. | |
| 2018/0082566 | A1 | 3/2018 | Semanoukian et al. | |
| 2018/0296124 | A1 | 10/2018 | Karakaya et al. | |
| 2019/0095586 | A1 | 3/2019 | Mcbrady et al. | |
| 2019/0143071 | A1 | 5/2019 | Alrefai et al. | |
| 2020/0188546 | A1 | 6/2020 | Hopkinson et al. | |
| 2020/0209136 | A1* | 7/2020 | Yee .................... | G01N 15/0625 |
| 2020/0330719 | A1 | 10/2020 | Segal et al. | |
| 2021/0369995 | A1 | 12/2021 | Kuzelka | |
| 2021/0379317 | A1 | 12/2021 | Cipollone et al. | |
| 2022/0020488 | A1 | 1/2022 | Kennedy et al. | |
| 2022/0023558 | A1 | 1/2022 | Benoit et al. | |
| 2022/0296844 | A1 | 9/2022 | Gonzalez | |
| 2022/0349593 | A1 | 11/2022 | Mou et al. | |
| 2022/0390135 | A1 | 12/2022 | Saravanan | |
| 2024/0068684 | A1* | 2/2024 | Avasthi .............. | G01N 33/0032 |
| 2024/0278044 | A1* | 8/2024 | Yee .................... | G01N 33/0073 |
| 2024/0325671 | A1* | 10/2024 | Avasthi .............. | G01N 33/0032 |
| 2025/0283622 | A1 | 9/2025 | Avasthi | |

FOREIGN PATENT DOCUMENTS

| | | | |
|---|---|---|---|
| CN | 105445156 | A | 12/2016 |
| CN | 116324373 | A | 6/2023 |
| EP | 2017586 | A1 | 1/2009 |
| EP | 3605059 | A1 | 2/2020 |
| EP | 4332568 | A1 | 3/2024 |
| JP | 2013-143957 | A | 7/2013 |
| JP | 2022-536584 | A | 8/2022 |
| KR | 10-0813679 | B1 | 3/2008 |
| KR | 10-2018-0028336 | A | 3/2018 |
| WO | 99/66304 | A1 | 12/1999 |
| WO | 2001/006248 | A3 | 5/2001 |
| WO | 2012/098303 | A1 | 7/2012 |
| WO | 2013/112287 | A1 | 8/2013 |
| WO | 2018/053433 | A1 | 3/2018 |
| WO | 2018/106809 | A3 | 12/2018 |
| WO | 2020/243369 | A1 | 12/2020 |
| WO | 2021/121736 | A1 | 6/2021 |
| WO | 2021/233957 | A1 | 11/2021 |
| WO | 2022/023958 | A1 | 2/2022 |
| WO | 2021/247716 | A3 | 3/2022 |
| WO | 2022/043664 | A2 | 3/2022 |
| WO | 2022/058967 | A1 | 3/2022 |
| WO | 2022/115899 | A1 | 6/2022 |

OTHER PUBLICATIONS

Notice of Allowance and Fees Due (PTOL-85) Mailed on May 14, 2024 for U.S. Appl. No. 17/822,857, 5 page(s).

Daniel Yee et al., U.S. Appl. No. 18/171,280 for "Air Quality Monitoring Device and Associated Method of Monitoring Air Quality", filed Feb. 17, 2023.

Rahul Avasthi et al., U.S. Appl. No. 18/052,666 for "Sensing and Secretion Bypass Apparatuses and Associated Methods", filed Nov. 24, 2022.

Rahul Avasthi, U.S. Appl. No. 17/822,857 for "Air Quality Monitoring Device and Associated Method of Manufacturing", filed Aug. 29, 2022.

Vyaire, "Vyaire™ Respiratory consumables catalog," 107 pages, (2017).

Decision to grant a European patent Mailed on Jul. 3, 2025 for EP Application No. 23203471, 2 page(s).

Extended European Search Report Mailed on Jun. 26, 2024 for EP Application No. 24156150, 12 page(s).

AU Notice of Allowance Mailed on Oct. 15, 2025 for AU Application No. 2024201235, 3 page(s).

CA Office Action Mailed on Aug. 29, 2025 for CA Application No. 3231444, 4 page(s).

English Translation of JP Office Action dated Aug. 25, 2025 for JP Application No. 2024036690, 4 page(s).

JP Office Action Mailed on Aug. 25, 2025 for JP Application No. 2024036690, 4 page(s).

Extended European Search Report Mailed on Jan. 9, 2024 for EP Application No. 23190674, 15 page(s).

Markes International, "Monitoring VOC emissions from respiratory medical devices in accordance with the new ISO 18562 international standard," Application Note 132, 1-10, (Aug. 2017).

Non-Final Rejection Mailed on Jan. 23, 2024 for U.S. Appl. No. 17/822,857, 6 page(s).

Philips, "Philips Respironics Update on PE-PUR Testing Results and Conclusions Available to Date," 1-31, (Jun. 28, 2022).

Verena S. Aichner, "How to sample and to analyse VOCs of respiratory medical devices according to the new ISO 18562-3," Pharmind, 80(10): 1423-1427, (Nov. 2018). [Retrieved from the Internet Jan. 23, 2024: URL: <https://cdnmedia.eurofins.com/eurofins-germany/media/2848741/pi8010_1561_aichner_10-18_05nov18.pdf>].

Wojciech Wojnowski et al., "Real-time monitoring of the emission of volatile organic compounds from polylactide 3D printing filaments," Science of the Total Environment, 805(1-7), (Sep. 14, 2021).

AU Office Action Mailed on Feb. 10, 2025 for AU Application No. 2024201235, 8 page(s).

CA Office Action Mailed on Jan. 28, 2025 for CA Application No. 3217903, 3 page(s).

Communication about intention to grant a European patent Mailed on Mar. 11, 2025 for EP Application No. 23203471, 5 page(s).

English Translation of JP Office Action dated Mar. 17, 2025 for JP Application No. 2024036690, 3 page(s).

EP Office Action Mailed on Apr. 16, 2025 for EP Application No. 24159481, 3 page(s).

Final Rejection Mailed on Mar. 4, 2025 for U.S. Appl. No. 18/052,666, 16 page(s).

JP Office Action Mailed on Mar. 17, 2025 for JP Application No. 2024036690, 3 page(s).

Examiner Interview Summary Record (PTOL-413) Mailed on Sep 20, 2024 for U.S. Appl. No. 17822857, 1 page(s)

Non-Final Rejection Mailed on Oct. 22, 2024 for U.S. Appl. No. 18/052,666, 12 page(s).

Notice of Allowance and Fees Due (PTOL-85) Mailed on Sep. 20, 2024 for U.S. Appl. No. 17/822,857, 9 page (s).

AU Office Action Mailed on Oct. 22, 2024 for AU Application No. 2024200764, 3 page(s).

Extended European Search Report Mailed on Aug. 14, 2024 for EP Application No. 24159481, 7 page(s).

Intention to grant Mailed on Nov. 24, 2025 for EP Application No. 23190674, 6 page(s).

Non-Final Rejection Mailed on Jan. 14, 2026 for U.S. Appl. No. 18/171,280, 71 page(s).

Non-Final Rejection Mailed on Feb. 25, 2026 for U.S. Appl. No. 18/989,720, 11 page(s).

CA Office Action Mailed on Feb. 16, 2026 for CA Application No. 3231444, 3 page(s).

Decision to grant a European patent Mailed on Mar. 26, 2026 for EP Application No. 23190674, 2 page(s).

English translation of JP Decision to Grant dated Mar. 17, 2026 for JP Application No. 2024036690, 2 page(s).

JP Decision to Grant Mailed on Mar. 17, 2026 for JP Application No. 2024036690, 3 page(s).

Notice of Allowance and Fees Due (PTOL-85) Mailed on Jun. 18, 2026 for U.S. Appl. No. 18/989,720, 5 page(s).

Non-Final Rejection Mailed on May 4, 2026 for U.S. Appl. No. 18/171,280, 80 page(s).

Intention to grant Mailed on May 11, 2026 for EP Application No. 24159481, 6 page(s).

* cited by examiner

AIR QUALITY ANALYSIS DEVICE

TECHNOLOGICAL FIELD

Embodiments of the present disclosure relate generally to an air quality analysis device and a method of performing air quality analysis.

BACKGROUND

Applicant has identified many technical challenges and difficulties associated with air quality analysis. Through applied effort, ingenuity, and innovation, Applicant has solved problems related to air quality analysis by developing solutions embodied in the present disclosure, which are described in detail below.

BRIEF SUMMARY

Various embodiments described herein relate to an air quality analysis device and a method of performing air quality analysis.

In accordance with one aspect of the disclosure, an air quality analysis device is provided. In some embodiments, air quality analysis device includes a housing having a chamber comprising an inlet port. In some embodiments, the inlet port is structured to receive an air flow into the chamber. In some embodiments, air quality analysis device includes a plurality of sensors disposed within the chamber and configured to generate air quality data associated with the air flow. In some embodiments, the plurality of sensors comprises at least one mold sensor. In some embodiments, air quality analysis device includes a printed circuit board in communication with the plurality of sensors and configured to transmit the air quality data to a computing device.

In some embodiments, the plurality of sensors further comprises at least one of a particulate matter sensor, a volatile organic compound sensor, a humidity sensor, or a temperature sensor.

In some embodiments, the particulate matter sensor is configured to generate air quality data indicating that there are particles having a diameter of less than 2.5 microns or 10 microns in the air flow.

In some embodiments, the plurality of sensors further comprises a first volatile organic compound sensor and a second volatile organic compound sensor.

In some embodiments, the first volatile organic compound sensor is configured to generate air quality data indicating that there is a first volatile organic compound in the air flow and the second volatile organic compound sensor is configured to generate air quality data indicating that there is a second volatile organic compound in the air flow.

In some embodiments, the at least one mold sensor comprises a spectrometer.

In some embodiments, the at least one mold sensor is configured to generate air quality data indicating a probability of mold being in the air flow based at least on a humidity associated with the air flow, a temperature associated with the air flow, a particle concentration associated with the air flow, and a cleaning date associated with the air flow.

In some embodiments, the chamber comprises an outlet port structured to discharge the air flow from the chamber.

In some embodiments, inlet port is structured to receive the air flow into the chamber from a tube associated with a continuous positive airway pressure machine and the outlet port is structured to discharge the air flow from the chamber into a face mask associated with the continuous positive airway pressure machine.

In some embodiments, inlet port is structured to receive the air flow into the chamber from a blower of a continuous positive airway pressure machine and the outlet port is structured to discharge the air flow from the chamber into a tube associated with the continuous positive airway pressure machine.

In some embodiments, the chamber comprises a first portion and a second portion.

In some embodiments, the plurality of sensors is disposed in the first portion.

In some embodiments, the computing device comprises a user interface configured display an instruction indicating that a user should clean a continuous positive airway pressure machine associated with the user.

In accordance with another aspect of the disclosure, a method of performing air quality analysis is provided. In some embodiments, the method of performing air quality analysis may include receiving air quality data from an air quality analysis device. In some embodiments, air quality analysis device includes a housing having a chamber comprising an inlet port. In some embodiments, the inlet port is structured to receive an air flow into the chamber. In some embodiments, air quality analysis device includes a plurality of sensors disposed within the chamber and configured to generate air quality data associated with the air flow. In some embodiments, the plurality of sensors comprises at least one mold sensor. In some embodiments, air quality analysis device includes a printed circuit board in communication with the plurality of sensors and configured to transmit the air quality data to a computing device. In some embodiments, the method of performing an air quality analysis may include causing a user interface to display an instruction to a user associated with a continuous positive airway pressure machine instructing the user to clean the continuous positive airway pressure machine.

In some embodiments, the plurality of sensors further comprises at least one of a particulate matter sensor, a volatile organic compound sensor, a humidity sensor, or a temperature sensor.

In some embodiments, the particulate matter sensor is configured to generate air quality data indicating that there are particles having a diameter of less than 2.5 microns or 10 microns in the air flow.

In some embodiments, the plurality of sensors further comprises a first volatile organic compound sensor and a second volatile organic compound sensor.

In some embodiments, the first volatile organic compound sensor is configured to generate air quality data indicating that there is a first volatile organic compound in the air flow and the second volatile organic compound sensor is configured to generate air quality data indicating that there is a second volatile organic compound in the air flow.

In some embodiments, the at least one mold sensor comprises a spectrometer.

In some embodiments, the at least one mold sensor is configured to generate air quality data indicating a probability of mold being in the air flow based at least on a humidity associated with the air flow, a temperature associated with the air flow, a particle concentration associated with the air flow, and a cleaning date associated with the air flow.

In some embodiments, the chamber comprises an outlet port structured to discharge the air flow from the chamber.

In some embodiments, inlet port is structured to receive the air flow into the chamber from a tube associated with the continuous positive airway pressure machine and the outlet port is structured to discharge the air flow from the chamber into a face mask associated with the continuous positive airway pressure machine.

In some embodiments, inlet port is structured to receive the air flow into the chamber from a blower of the continuous positive airway pressure machine and the outlet port is structured to discharge the air flow from the chamber into a tube associated with the continuous positive airway pressure machine.

In some embodiments, the chamber comprises a first portion and a second portion.

In some embodiments, the plurality of sensors is disposed in the first portion.

The above summary is provided merely for purposes of summarizing some example embodiments to provide a basic understanding of some aspects of the present disclosure. Accordingly, it will be appreciated that the above-described embodiments are merely examples and should not be construed to narrow the scope or spirit of the disclosure in any way. It will be appreciated that the scope of the present disclosure encompasses many potential embodiments in addition to those here summarized, some of which will be further described below.

BRIEF DESCRIPTION OF THE DRAWINGS

Reference will now be made to the accompanying drawings. The components illustrated in the figures may or may not be present in certain embodiments described herein. Some embodiments may include fewer (or more) components than those shown in the figures in accordance with an example embodiment of the present disclosure.

DETAILED DESCRIPTION

Figure 1:
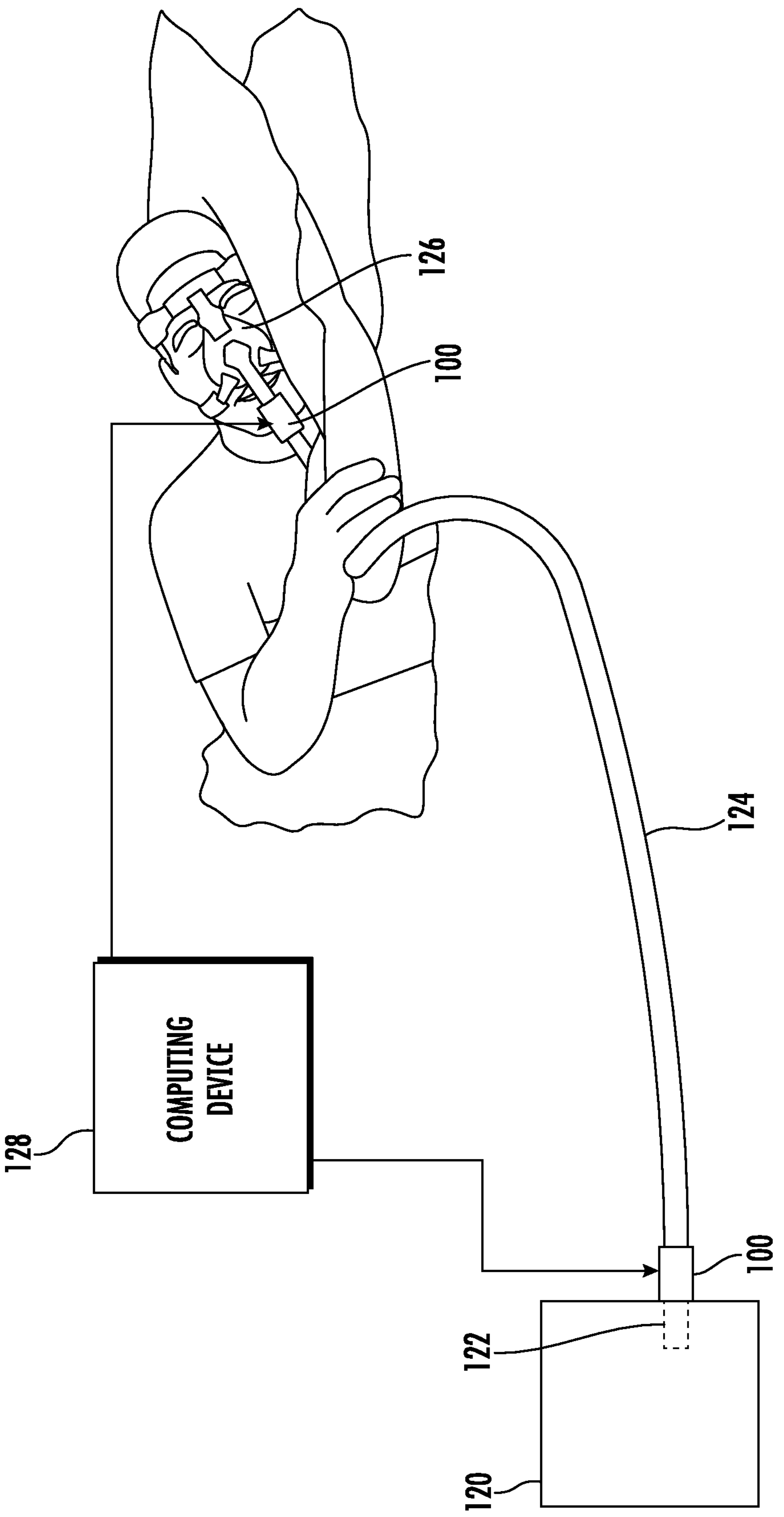
FIG. 1 illustrates an example air quality analysis device in accordance with one or more embodiments of the present disclosure.

Example embodiments will be described more fully hereinafter with reference to the accompanying drawings, in which some, but not all embodiments of disclosure are shown. Indeed, embodiments of the disclosure may be embodied in many different forms and should not be construed as limited to the embodiments set forth herein; rather, these embodiments are provided so that this disclosure will satisfy applicable legal requirements. Like numbers refer to like elements throughout.

Overview

Example embodiments disclosed herein address technical problems associated with air quality analysis devices and methods of performing air quality analysis. As would be understood by one skilled in the field to which this disclosure pertains, there are numerous example scenarios in which a user may use an air quality analysis device and methods of performing air quality analysis. For example, it may be necessary to use an air quality analysis device to generate air quality data of air flow associated with a continuous positive airway pressure (CPAP) machine that indicates that there is a probably of mold being in the air flow and/or the CPAP machine.

A CPAP machine, for example, provides a flow of pressurized air that, in some examples, is also heated and humified, to a user's upper airway while the user is sleeping to ensure that the user's upper airway is not obstructed so the user can obtain enough oxygen while sleeping. In some examples, due to the frequent use of CPAP machines (e.g., every night), the humidification of the air flow, the heating of the air flow, and/or infrequent cleaning by a user of the CPAP machine, CPAP machines often develop mold, resulting in the user being exposed to mold when using the CPAP machine. Accordingly, there is a need for devices and methods that can generate air quality data associated with the air flow provided by CPAP machines to users to ensure that the users do not breath in air flow having mold in it.

Thus, to address these and/or other related issues, an air quality analysis device and a method of performing air quality analysis are disclosed herein. For example, an embodiment in this disclosure, described in greater detail below, includes an air quality analysis device having a housing having a chamber comprising an inlet port. In some embodiments, the inlet port is structured to receive an air flow into the chamber. In some embodiments, the air quality analysis device may include a plurality of sensors disposed within the chamber and configured to generate air quality data associated with the air flow. In some embodiments, the plurality of sensors comprises at least one mold sensor. In some embodiments, the air quality analysis device may include a printed circuit board in communication with the plurality of sensors and configured to transmit the air quality data to a computing device. As such, the air quality of air flow provided by CPAP machines may be analyzed to ensure that a user of the CPAP machine does not breath in air flow provided by the CPAP machine having mold in it.

Example Air Quality Analysis Device

With reference to FIGS. 1-5, embodiments herein provide for an example air quality analysis device 100. The air quality analysis device 100 may be configured to generate air quality data associated with an air flow. In some embodiments, such as illustrated in FIG. 1, the air quality analysis device 100 may be configured to generate air quality data associated with air flow provided by a continuous positive pressure machine (CPAP) machine 120. Although referred to herein as performing air quality analysis associated with airflow provided by a CPAP machine, it would be understood by one skilled in the field to which this disclosure pertains that the air quality analysis device 100 may be used to generate air quality data associated with air flow provided by any type of positive airway pressure machine, such as automatic positive airway pressure (APAP) machines, bilevel positive airway pressure (BiPAP) machines, adaptive servo-ventilation (ASV) machines, other mechanical ventilation machines, and/or the like.

In some embodiments, the air quality analysis device 100 may include a housing 102. The housing 102 may be substantially cubical, substantially rectangular, and/or substantially cylindrical. In some embodiments, the housing 102 may include a chamber 104. The chamber 104 may be substantially cubical, substantially rectangular, and/or substantially cylindrical. In some embodiments, the chamber 104 may be substantially the same shape as the housing 102. In some embodiments, the chamber 104 may not be substantially the same shape as the housing 102. In some embodiments, the housing 102 and/or the chamber 104 may be comprised of plastic or any other suitable material. In some embodiments, the housing 102 and/or the chamber 104 may be constructed using injection molding and/or 3D printing.

In some embodiments, the chamber 104 may have an inlet port 106 and/or an outlet port 108. In this regard, for example, the inlet port 106 may be configured to receive air flow into the chamber 104 and the outlet port 108 may be configured to discharge air flow into the chamber 104 (e.g., the air flow moves through the chamber 104 from the inlet port 106 to the outlet port 108). In some embodiments, the inlet port 106 may be structured to receive the air flow into the chamber 104 from a blower 122 of the CPAP machine 120 and the outlet port 108 may be structured to discharge the air to a tube 124 associated with the CPAP machine 120 (e.g., the inlet port 106 may be structured to be attached to the blower 122 of the CPAP machine 120 and the outlet port 108 may be structured to be attached to the tube 124 associated with the CPAP machine 120). Additionally or alternatively, the inlet port 106 may be structured to receive the air flow into the chamber 104 from the tube 124 of the CPAP machine 120 and the outlet port 108 may be structured to discharge the air to a face mask 126 associated with the CPAP machine 120 (e.g., the inlet port 106 may be structured to be attached to the tube 124 of the CPAP machine 120 and the outlet port 108 may be structured to be attached to the face mask 126 associated with the CPAP machine 120).

Figure 2:
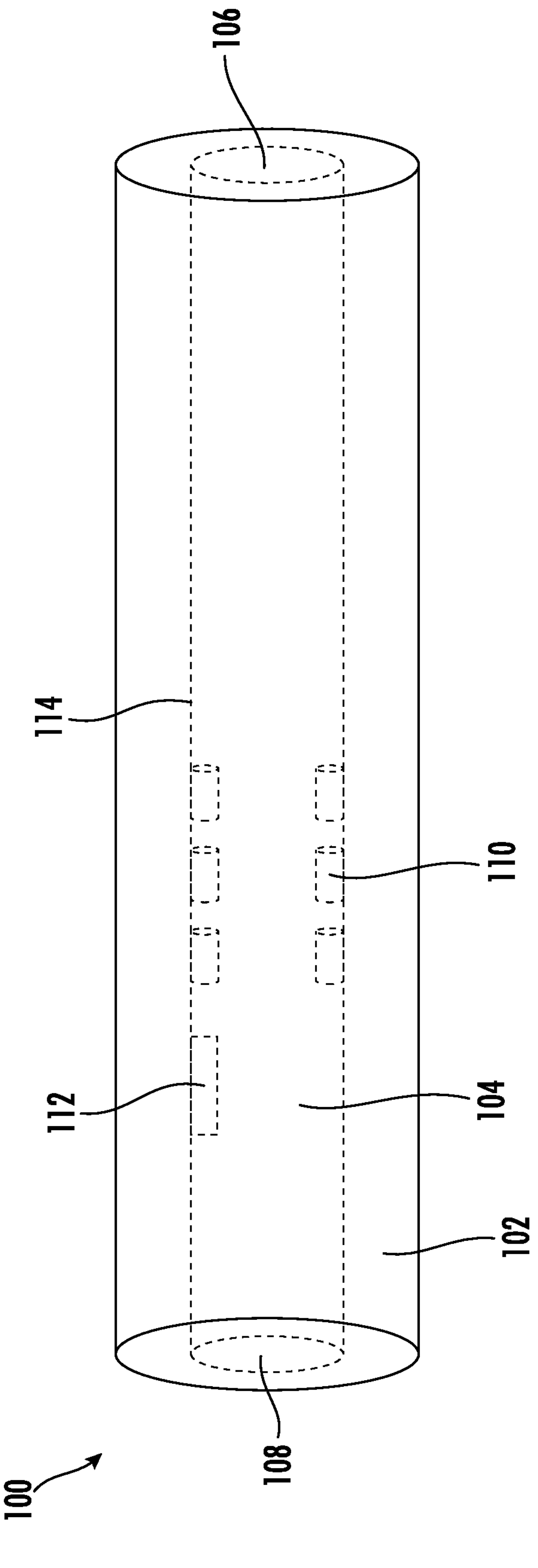
FIG. 2 illustrates a side view of the example air quality analysis device in accordance with one or more embodiments of the present disclosure.
Figure 3:
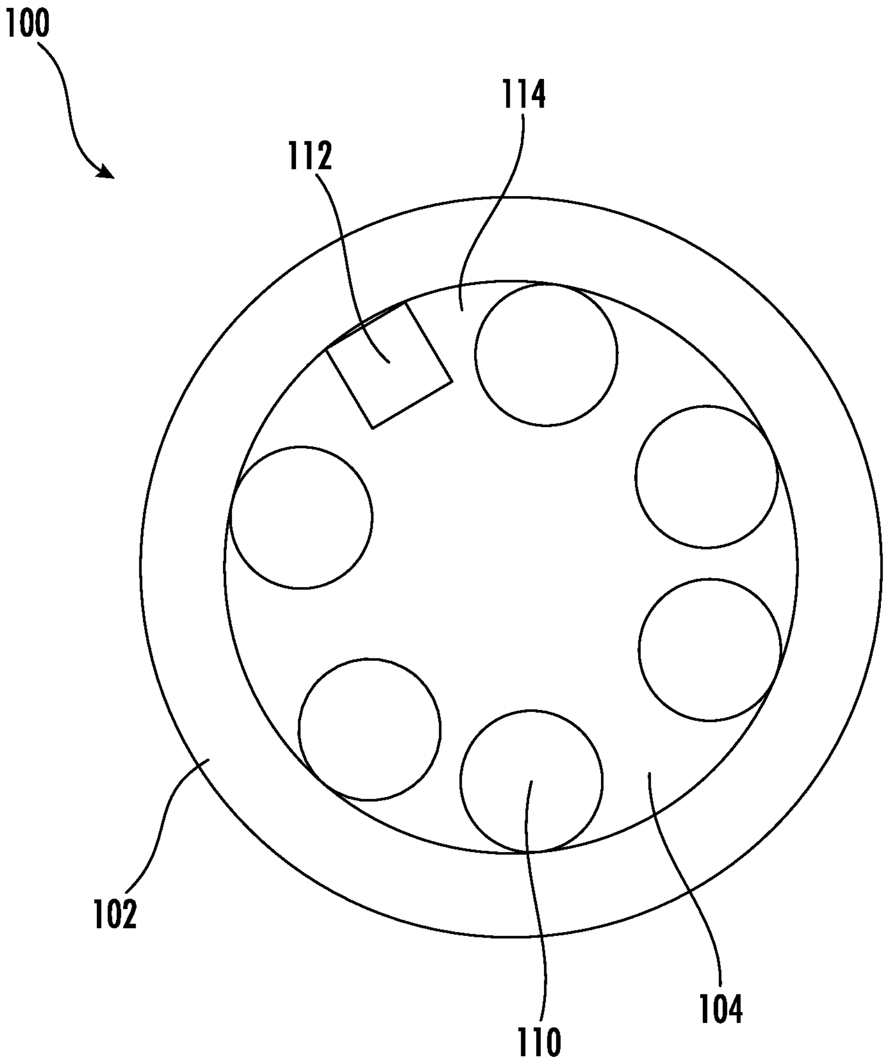
FIG. 3 illustrates a cross-sectional view of the example air quality analysis device in accordance with one or more embodiments of the present disclosure.
Figure 4:
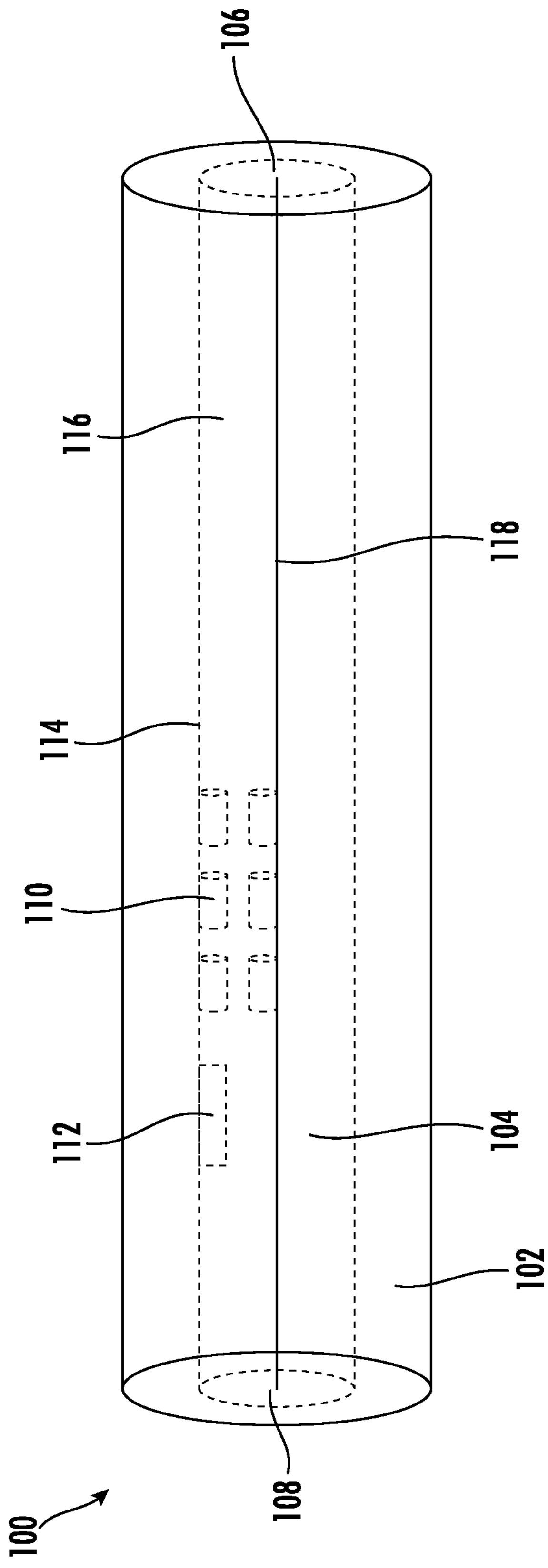
FIG. 4 illustrates another side view of the example air quality analysis device in accordance with one or more embodiments of the present disclosure.
Figure 5:
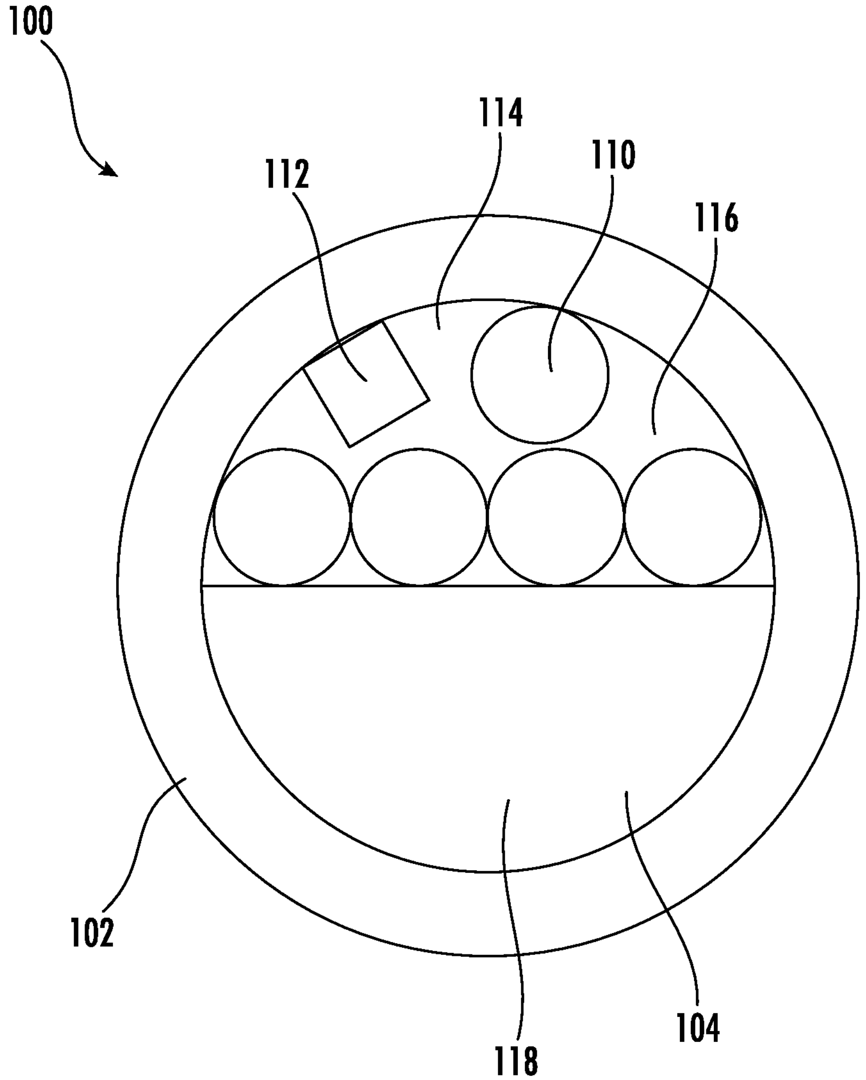
FIG. 5 illustrates another cross-sectional view of the example air quality analysis device in accordance with one or more embodiments of the present disclosure.

In some embodiments, the air quality analysis device 100 may include a plurality of sensors 110 disposed in the chamber 104. The plurality of sensors 110 may be disposed in the chamber 104 in any manner that enables the plurality of sensors 110 to generate air quality data associated with the air flow. Said differently, for example, the plurality of sensors 110 may be disposed in the chamber 104 in any manner that enables each of the plurality of sensors 110 to be able to interact with the air flow such that each of the plurality of sensors 110 can generate air quality data associated with the air flow. For example, such as illustrated in FIGS. 2 and 3, the plurality of sensors 110 may be disposed on an interior surface 114 of the chamber 104. As another example, such as illustrated in FIGS. 4 and 5, the plurality of sensors 110 may be disposed in a first portion 116 of the chamber 104. That is, the plurality of sensors 110 may all be disposed in a first portion 116 of the chamber 104 and none of the plurality of sensors 110 may be disposed in a second portion 118 of the chamber 104.

In some embodiments, the plurality of sensors 110 may be configured to generate air quality data associated with the air flow. In this regard, for example, the plurality of sensors 110 may be configured to generate air quality data associated with the air flow by generating air quality data indicating a probability of mold in the air flow, generating air quality data indicating that there are particles in the air flow having a particular size, generating air quality data indicating volatile organic compounds in the air flow, generating air quality data indicating a humidity associated with the air flow, and/or generating air quality data indicating a temperature associated with the air flow. In some embodiments, if the plurality of sensors 110, based on the air quality data generated by the plurality of sensors 110, determine a probability that mold is present in the air flow, particles of a particular size are present in the air flow, and/or volatile organic compounds are in the air flow. In this regard, for example, the air quality data may indicate that mold, particles of a particular size, and/or volatile organic compounds are present in the CPAP machine 120, the tube 124, and/or the face mask 126.

In some embodiments, the plurality of sensors 110 may include at least one mold sensor. In this regard, for example, the plurality of sensors 110 may include at least one mold sensor configured to generate air quality data indicating a probability of mold in the air flow (e.g., is mold present in the air flow). In some embodiments, the at least one mold sensor may include a spectrometer configured to generate air quality data indicating a probability of mold in the air flow. Additionally or alternatively, the at least one mold sensor may be configured to generate air quality data indicating a probability of mold in the air flow based on one or more of humidity associated with the air flow, a temperature associated with the air flow, a particle concentration associated with the air flow, and a cleaning date associated with the air flow. For example, the mold sensor may be configured to generate air quality data that there is a probability mold in the air flow when the humidity associated with the air flow is a above a humidity threshold (e.g., above 95%) and the cleaning date associated with the air flow indicates that it has been a greater amount of time than a cleaning time threshold (e.g., it has been 6 months since the CPAP Machine 120 has been cleaned and the cleaning time threshold is 3 months). In this regard, for example, In some embodiments, based on the generated air quality data, the at least one mold sensor may be configured to determine that the probability mold is present in the air flow is low, medium, or high that mold is present in the air flow.

In some embodiments, the plurality of sensors 110 may include at least one particulate matter sensor. In this regard, for example, the plurality of sensors 110 may include at least one particulate matter sensor configured to generate air quality data indicating that there are particles in the air flow (e.g., how many particles in the air flow, concentration of particles in the air flow, size of particles in the air flow, etc.), such as particles having a diameter of less than 2.5 microns and/or 10 microns. In this regard, for example, the plurality of sensors 110 may include a first particulate matter sensor to generate air quality data indicating that there are particles having a diameter of 2.5 microns or less and/or a second particulate matter sensor to generate air quality data indicating that there are particles having a diameter of 10 microns or less. In some embodiments, the plurality of sensors 110 may include a particulate matter sensor that is configured to generate air quality data indicating that there are multiple particles of multiple diameters, such as a particulate matter sensor that can generate air quality data indicating that there are particles having a diameter of 2.5 microns or less and/or particles have a diameter of 10 microns or less.

In some embodiments, the plurality of sensors 110 may include at least one volatile organic compound sensor. In this regard, for example, the plurality of sensors 110 may include at least one volatile organic compound sensor that configured to generate air quality data indicating volatile organic compounds in the air flow, such as one or more of benzene, ethylene glycol, formaldehyde, acetone, methylene chloride, tetrachloroethylene, toluene, xylene, and/or 1,3-butadiene. In some embodiments, the plurality of sensors 110 may include volatile organic compound sensors that are each configured to generate air quality data indicating that there are a specific volatile organic compound is in the air flow. For example, the plurality of sensors 110 may include a first volatile organic compound sensor configured to generate air quality data indicating that there is a first volatile organic compound in the air flow, such as benzene, and a second volatile organic compound sensor configured to generate air quality data indicating that there is a second volatile organic compound, such as acetone. In some embodiments, the plurality of sensors 110 may include a volatile organic compound sensor that is configured to generate air quality data indicating that there are more than one volatile organic compound in the air flow.

In some embodiments, the plurality of sensors 110 may include at least one humidity sensor. In this regard, for example, the plurality of sensors 110 may include at least one humidity sensor that can generate air quality data indicating a humidity associated with the air flow. For example, the at least one humidity sensor may generate air quality data indicating that the air flow is associated with a 90% humidity. In some embodiments, the plurality of sensors 110 may include at least one temperature sensor. In this regard, for example, the plurality of sensors 110 may include at least one temperature sensor that can generate air quality data indicating a temperature associated with the air flow. For example, the at least one temperature sensor may generate air quality data indicating that the air flow has a temperature of 90 degrees.

In some embodiments, the air quality data generated by the plurality of sensors 110 may be obtained and stored in a structured and/or in an unstructured data format. For example, the air quality data may indicate that the probability of mold being in the air flow is low, medium, or high mold is present in the air flow based on the air quality data generated made by the mold sensor. As another example, the air quality data may include a count of the number of times the at least one particulate matter sensor generated air quality data indicating that particles of a particular size are in the air flow (e.g., the at least one particulate matter sensor counted 25 particles with a size of 2.5 microns or less in the air flow). As another example, the air quality data may include an indication of whether or not the at least one volatile organic compound sensor generated air quality data indicating that a specific volatile organic compound is in the air flow (e.g., the at least one volatile organic compound sensor generated air quality data indicating that formaldehyde is in the air flow). As another example, the air quality data may include a temperature and a humidity associated with the air flow as generated by the at least one temperature sensor and/or humidity sensor.

In some embodiments, the air quality analysis device 100 may include a printed circuit board (PCB) 112. In some embodiments, the PCB 112 may be disposed proximate the plurality of sensors 110. For example, if the plurality of sensors 110 is disposed on the interior surface 114 of the chamber 104, such as illustrated in FIGS. 2 and 3, the PCB 112 may be disposed on the interior surface 114 of the chamber 104. Additionally or alternatively, if the plurality of sensors is disposed in the first portion 116 of the chamber 104, such as illustrated in FIGS. 4 and 5, the PCB may be disposed in the first portion 116 of the chamber 104.

In some embodiments, the PCB 112 may be in electrical communication with the plurality of sensors 110 and be configured to transmit the air quality data generated by the plurality of sensors 110 to a computing device 128. In some embodiments, the PCB 112 may transmit the air quality data generated by the plurality of sensors 110 to the computing device 128 via Wi-Fi and/or Bluetooth. In some embodiments, the PCB 112 may be configured to transmit the air quality data to the computing device in real-time. For example, each time the at least one volatile organic compound sensor generated air quality data indicating that a volatile organic compound is in the air flow, the PCB 112 may transmit generated air quality data to the computing device 128.

In some embodiments, the PCB 112 may be configured to transmit the air quality data to the computing device 128 on a pre-determined schedule. For example, the PCB 112 may transmit the air quality data to the computing device 128 every 20 seconds. In some embodiments, the PCB 112 may be configured to transmit the air quality data to the computing device 128 at the end of an analysis period. For example, the PCB 112 may be configured to identify when air flow has started flowing through the chamber 104 and when air flow has stopped flowing through the chamber 104. In this regard, when the PCB 112 has identified that the air flow has stopped flowing through the chamber 104, the PCB 112 may transmit the air quality data to the computing device 128. In some embodiments, the PCB 112 may be configured to transmit the air quality data to the computing device 128 upon receiving an instruction to transmit the air quality data from the computing device 128.

Figure 6:
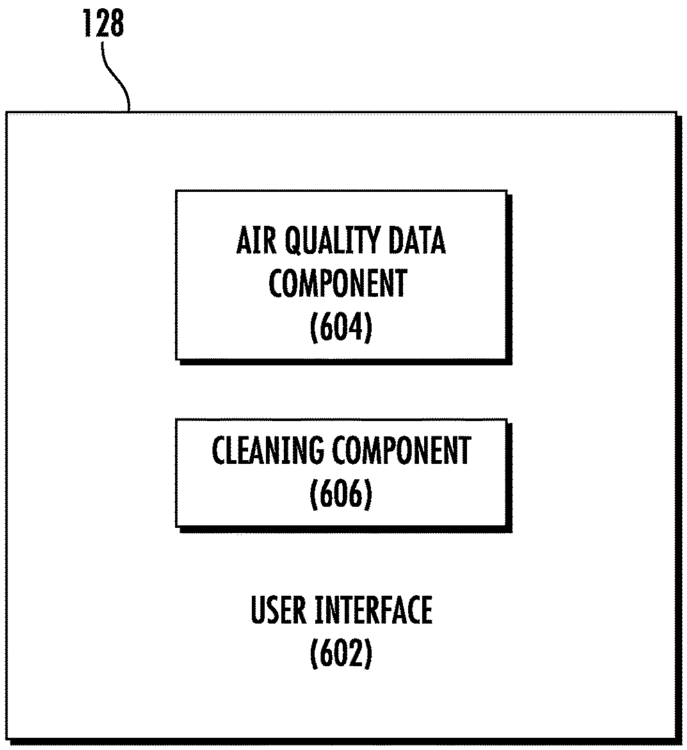
FIG. 6 illustrates an example user interface of a computing device in accordance with one or more embodiments of the present disclosure.

With reference to FIG. 6, in some embodiments, the computing device 128 may include a user interface 602. In some embodiments, the user interface 602 may be provided by a mobile application executing on the computing device 128. In some embodiments, the user interface 602 may include an air quality data component 604 configured to indicate air quality data generated by the plurality of sensors 110. For example, the air quality data component 604 may indicate that the probability that there is mold in the air flow is low, medium, or high, the CPAP machine 120, the tube 124, and/or the face mask 126 if the at least one mold sensor determines that the probability that there is mold in the air flow is low, medium, or high. As another example, the air quality data component 604 may indicate a count of the number of times the at least one particulate matter sensor generated air quality data indicating particles of a particular size and the size of the particles in the air flow, the CPAP machine 120, the tube 124, and/or the face mask 126 if the at least one particulate matter sensor determines a count of the number of times the at least one particulate matter sensor generated air quality data indicating particles of a particular size and the size of the particles in the air flow. As another example, the air quality data component 604 may indicate that there is an at least one volatile organic compound sensor in the air flow, the CPAP machine 120, the tube 124, and/or the face mask 126 if the at least one volatile organic compound sensor generated air quality data indicating a specific volatile organic compound is in the air flow (e.g., the at least one volatile organic compound sensor generated air quality data indicating formaldehyde is in the air flow). As another example, the air quality data component 604 may indicate a humidity and/or temperature associated with the air flow the CPAP machine 120, the tube 124, and/or the face mask 126 based on air quality data indicating a humidity of the air flow generated by the at least one humidity sensor and/or air quality data indicating a temperature of the air flow generated by the at least one temperature sensor.

In some embodiments, the user interface 602 may include a cleaning component 606 configured to display an instruction indicating that the CPAP machine 120, the tube 124, and/or the face mask 126 should be cleaned. For example, the cleaning component 606 may display an instruction indicating that the CPAP machine 120, the tube 124, and/or the face mask 126 should be cleaned if the probability that mold is present in the air flow, the CPAP machine 120, the tube 124, and/or the face mask 126 is medium or high. As another example, the cleaning component 606 may display an instruction indicating that the CPAP machine 120, the tube 124, and/or the face mask 126 should be cleaned if a count of the number of times the at least one particulate matter sensor generated air quality data indicating particles of a particular size in the air flow the CPAP machine 120, the tube 124, and/or the face mask 126 is above a particle threshold. As another example, the cleaning component 606 may display an instruction indicating that the CPAP machine 120, the tube 124, and/or the face mask 126 should be cleaned if the at least one volatile organic compound sensor generated air quality data indicating a specific volatile organic compound (e.g., the at least one volatile organic compound sensor generated air quality data indicating formaldehyde is in the air flow) is in the air flow. As another example, the cleaning component 606 may display an instruction indicating that the CPAP machine 120, the tube 124, and/or the face mask 126 should be cleaned if a temperature and a humidity and/or temperature associated with the air flow the CPAP machine 120, the tube 124, and/or the face mask 126 if a humidity of the air flow is above a humidity threshold and/or a temperature of the air flow is above a temperature threshold.

Example Method of Performing Air Quality Analysis

Figure 7:
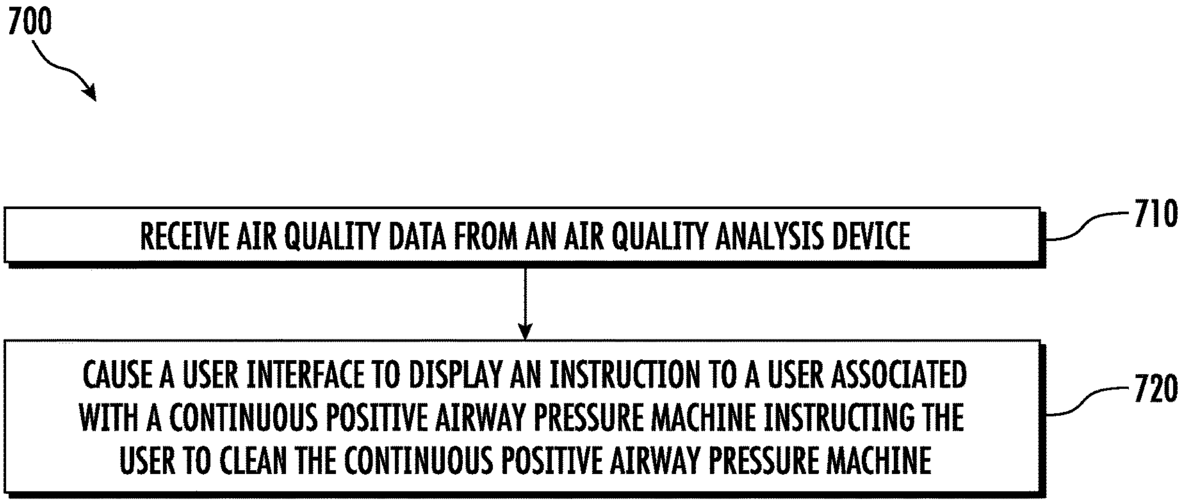
FIG. 7 illustrates a flowchart of an example method of performing air quality analysis in accordance with one or more embodiments of the present disclosure.

Referring now to FIG. 7, a flowchart providing an example method 700 of performing air quality analysis is illustrated. In this regard, FIG. 7 illustrates operations that may be performed by the computing device 128 and/or the air quality analysis device 100.

As shown in block 710, the method 700 of performing air quality analysis may include receiving air quality data from an air quality analysis device. As described above, the air quality analysis device may include a housing. In some embodiments, the housing may include a chamber. In some embodiments, the housing and/or the chamber may be comprised of plastic or any other suitable material. In some embodiments, the housing and/or the chamber may be constructed using injection molding and/or 3D printing.

In some embodiments, the chamber may have an inlet port and/or an outlet port. In this regard, for example, the inlet port may be configured to receive air flow into the chamber and the outlet port may be configured to discharge air flow into the chamber (e.g., the air flow moves through the chamber from the inlet port to the outlet port). In some embodiments, the inlet port may be structured to receive the air flow into the chamber from a blower of the CPAP machine and the outlet port may be structured to discharge the air to a tube associated with the CPAP machine (e.g., the inlet port may be structured to be attached to the blower of the CPAP machine and the outlet port may be structured to be attached to the tube associated with the CPAP machine). Additionally or alternatively, the inlet port may be structured to receive the air flow into the chamber from the tube of the CPAP machine and the outlet port may be structured to discharge the air to a face mask associated with the CPAP machine (e.g., the inlet port may be structured to be attached to the tube of the CPAP machine and the outlet port may be structured to be attached to the face mask associated with the CPAP machine).

As described above, in some embodiments, the air quality analysis device may include a plurality of sensors disposed in the chamber. The plurality of sensors may be disposed in the chamber in any manner that enables the plurality of sensors to generate air quality data associated with the air flow. Said differently, for example, the plurality of sensors may be disposed in the chamber in any manner that enables each of the plurality of sensors to be able to interact with the air flow such that each of the plurality of sensors can generate air quality data associated with the air flow. For example, the plurality of sensors may be disposed on an interior surface of the chamber. As another example, the plurality of sensors may be disposed in a first portion of the chamber. That is, the plurality of sensors may all be disposed in a first portion of the chamber and none of the plurality of sensors may be disposed in a second portion of the chamber.

As described above, in some embodiments, the plurality of sensors may be configured to generate air quality data associated with the air flow. In this regard, for example, the plurality of sensors may be configured to generate air quality data associated with the air flow by generating air quality data indicating that there is a probability of mold in the air flow, generating air quality data indicating particles in the air flow having a particular size, generating air quality data indicating volatile organic compounds in the air flow, generating air quality data indicating a humidity associated with the air flow, and/or generating air quality data indicating a temperature associated with the air flow. In some embodiments, if the plurality of sensors, based on air quality data generated by the plurality of sensors, determine that a probability of mold being in the air flow, particles of a particular size are present in the air flow, and/or volatile organic compounds are in the air flow, it may indicate that mold, particles of a particular size, and/or volatile organic compounds are present in the CPAP machine, the tube, and/or the face mask.

As described above, in some embodiments, the air quality data generated by the plurality of sensors may be obtained and stored in a structured and/or in an unstructured data format. In some embodiments, the air quality analysis device may include a printed circuit board (PCB). In some embodiments, the PCB may be disposed proximate the plurality of sensors. For example, if the plurality of sensors is disposed on the interior surface of the chamber the PCB may be disposed on the interior surface of the chamber. Additionally or alternatively, if the plurality of sensors is disposed in the first portion of the chamber the PCB may be disposed in the first portion of the chamber.

As described above, in some embodiments, the PCB may be in electrical communication with the plurality of sensors and be configured to transmit the air quality data generated by the plurality of sensors to a computing device and the computing device may be configured to receive the air quality data from the PCB. In some embodiments, the PCB may transmit the air quality data generated by the plurality of sensors to the computing device via Wi-Fi and/or Bluetooth.

As shown in block 720, the method 700 of performing air quality analysis may include causing a user interface to display an instruction to a user associated with a continuous positive airway pressure machine instructing the user to clean the continuous positive airway pressure machine.

As described above, in some embodiments, the user interface may include a cleaning component configured to display an instruction indicating that the CPAP machine, the tube, and/or the face mask should be cleaned. For example, the cleaning component may display an instruction indicating that the CPAP machine, the tube, and/or the face mask should be cleaned if the probability that mold is present in the air flow is medium or high in the air flow, the CPAP machine, the tube, and/or the face mask. As another example, the cleaning component may display an instruction indicating that the CPAP machine, the tube, and/or the face mask should be cleaned if the air quality data generated by the at least one particulate matter sensor indicates a count of the particles of a particular size in the air flow the CPAP machine, the tube, and/or the face mask is above a particle threshold. As another example, the cleaning component may display an instruction indicating that the CPAP machine, the tube, and/or the face mask should be cleaned if the at least one volatile organic compound sensor generated air quality data indicating a specific volatile organic compound (e.g., the at least one volatile organic compound sensor generated air quality data indicating formaldehyde is in the air flow) in the air flow. As another example, the cleaning component may display an instruction indicating that the CPAP machine, the tube, and/or the face mask should be cleaned if a temperature and a humidity and/or temperature associated with the air flow the CPAP machine, the tube, and/or the face mask if a humidity of the air flow is above a humidity threshold and/or a temperature of the air flow is above a temperature threshold.

Example Computer Processing Device

Figure 8:
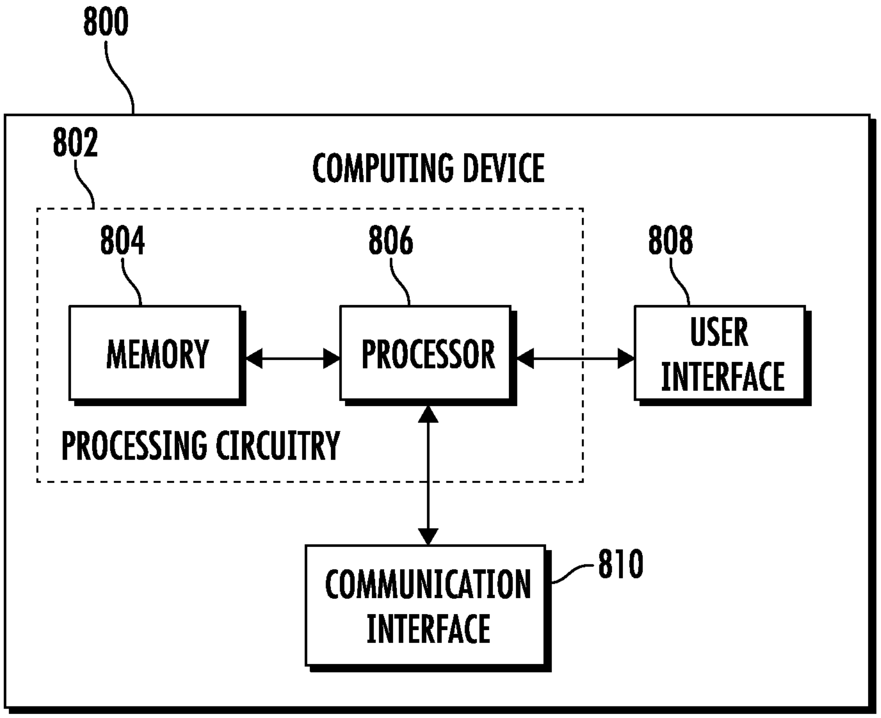
FIG. 8 illustrates a block diagram of an example computer processing device in accordance with one or more embodiments of the present disclosure.

With reference to FIG. 8, a block diagram of an example computer processing device 800 is illustrated in accordance with some example embodiments. In some embodiments, the PCB 112, the computing device 128, and/or other devices may be embodied as one or more computer processing devices, such as the computer processing device 800 in FIG. 8. However, it should be noted that the components, devices, or elements illustrated in and described with respect to FIG. 8 below may not be mandatory and thus one or more may be omitted in certain embodiments. Additionally, some embodiments may include further or different components, devices or elements beyond those illustrated in and described with respect to FIG. 8.

The computer processing device 800 may include or otherwise be in communication with processing circuitry 802 that is configurable to perform actions in accordance with one or more embodiments disclosed herein. In this regard, the processing circuitry 802 may be configured to perform and/or control performance of one or more functionalities of the computer processing device 800 in accordance with various embodiments, and thus may provide means for performing functionalities of the computer processing device 800 in accordance with various embodiments. The processing circuitry 802 may be configured to perform data processing, application execution and/or other processing and management services according to one or more embodiments. In some embodiments, the computer processing device 800 or a portion(s) or component(s) thereof, such as the processing circuitry 802, may be embodied as or comprise a chip or chip set. In other words, the computer processing device 800 or the processing circuitry 802 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The computer processing device 800 or the processing circuitry 802 may therefore, in some cases, be configured to implement an embodiment of the disclosure on a single chip or as a single "system on a chip." As such, in some cases, a chip or chipset may constitute means for performing one or more operations for providing the functionalities described herein.

In some embodiments, the processing circuitry 802 may include a processor 806 and, in some embodiments, such as that illustrated in FIG. 8, may further include memory 804. The processing circuitry 802 may be in communication with or otherwise control a user interface 808 and/or a communication interface 810. As such, the processing circuitry 802 may be embodied as a circuit chip (e.g., an integrated circuit chip) configured (e.g., with hardware, software or a combination of hardware and software) to perform operations described herein.

The processor 806 may be embodied in a number of different ways. For example, the processor 806 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor 806 may comprise a plurality of processors. The plurality of processors may be in operative communication with each other and may be collectively configured to perform one or more functionalities of the computer processing device 800 as described herein. In some embodiments, the processor 806 may be configured to execute instructions stored in the memory 804 or otherwise accessible to the processor 806. As such, whether configured by hardware or by a combination of hardware and software, the processor 806 may represent an entity (e.g., physically embodied in circuitry—in the form of processing circuitry 802) capable of performing operations according to embodiments of the present disclosure while configured accordingly. Thus, for example, when the processor 806 is embodied as an ASIC, FPGA or the like, the processor 806 may be specifically configured hardware for conducting the operations described herein. Alternatively, as another example, when the processor 806 is embodied as an executor of software instructions, the instructions may specifically configure the processor 806 to perform one or more operations described herein.

In some embodiments, the memory 804 may include one or more non-transitory memory devices such as, for example, volatile and/or non-volatile memory that may be either fixed or removable. In this regard, the memory 804 may comprise a non-transitory computer-readable storage medium. It will be appreciated that while the memory 804 is illustrated as a single memory, the memory 804 may comprise a plurality of memories. The memory 804 may be configured to store information, data, applications, instructions and/or the like for enabling the computer processing device 800 to carry out various functions in accordance with one or more embodiments. For example, the memory 804 may be configured to buffer input data for processing by the processor 806. Additionally or alternatively, the memory 804 may be configured to store instructions for execution by the processor 806. As yet another alternative, the memory 804 may include one or more databases that may store a variety of files, contents or data sets. Among the contents of the memory 804, applications may be stored for execution by the processor 806 in order to carry out the functionality associated with each respective application. In some cases, the memory 804 may be in communication with one or more of the processor 806, user interface 808, and/or communication interface 810 via a bus(es) for passing information among components of the computer processing device 800.

The user interface 808 may be in communication with the processing circuitry 802 to receive an indication of a user input at the user interface 808 and/or to provide an audible, visual, mechanical or other output to the user. As such, the user interface 808 may include, for example, a keyboard, a mouse, a joystick, a display, a touch screen display, a microphone, a speaker, and/or other input/output mechanisms. As such, the user interface 808 may, in some embodiments, provide means for a user to access and interact with the PCB 112 and/or the computing device 128.

The communication interface 810 may include one or more interface mechanisms for enabling communication with other devices and/or networks. In some cases, the communication interface 810 may be any means such as a device or circuitry embodied in either hardware, or a combination of hardware and software that is configured to receive and/or transmit data from/to a network and/or any other device or module in communication with the processing circuitry 802. By way of example, the communication interface 810 may be configured to enable the PCB 112 to communicate with the computing device 128 and/or computing devices. Accordingly, the communication interface 810 may, for example, include an antenna (or multiple antennas) and supporting hardware and/or software for enabling communications with a wireless communication network (e.g., a wireless local area network, cellular network, global positing system network, and/or the like) and/or a communication modem or other hardware/software for supporting communication via cable, digital subscriber line (DSL), universal serial bus (USB), Ethernet or other methods.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure.

Use of broader terms such as "comprises," "includes," and "having" should be understood to provide support for narrower terms such as "consisting of," "consisting essentially of," and "comprised substantially of" Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

That which is claimed:

1. An air quality analysis device, the air quality analysis device comprising:

a housing having a chamber comprising an inlet port, wherein the inlet port is structured to receive an air flow into the chamber;

a plurality of sensors disposed within the chamber, wherein the plurality of sensors comprises at least one mold sensor, wherein the at least one mold sensor is configured to generate air quality data of a respiratory support apparatus based at least on a cleaning date associated with the respiratory support apparatus; and a printed circuit board in communication with the plurality of sensors and configured to transmit the air quality data to a computing device.

2. The air quality analysis device of claim 1, wherein the plurality of sensors further comprises at least one of a particulate matter sensor, a volatile organic compound sensor, a humidity sensor, or a temperature sensor.

3. The air quality analysis device of claim 2, wherein the particulate matter sensor is configured to generate air quality data indicating that there are particles having a diameter of less than 2.5 microns or 10 microns in the air flow.

4. The air quality analysis device of claim 1, wherein the plurality of sensors further comprises a first volatile organic compound sensor and a second volatile organic compound sensor, wherein the first volatile organic compound sensor is configured to generate air quality data indicating that there is a first volatile organic compound in the air flow and the second volatile organic compound sensor is configured to generate air quality data indicating that there is a second volatile organic compound in the air flow.

5. The air quality analysis device of claim 1, wherein the at least one mold sensor comprises a spectrometer.

6. The air quality analysis device of claim 1, wherein the chamber comprises an outlet port structured to discharge the air flow from the chamber.

7. The air quality analysis device of claim 6, wherein the inlet port is structured to receive the air flow into the chamber from a tube associated with the respiratory support apparatus and the outlet port is structured to discharge the air flow from the chamber into a face mask associated with the respiratory support apparatus.

8. The air quality analysis device of claim 6, wherein the inlet port is structured to receive the air flow into the chamber from a blower of the respiratory support apparatus and the outlet port is structured to discharge the air flow from the chamber into a tube associated with the respiratory support apparatus.

9. The air quality analysis device of claim 1, wherein the chamber comprises a first portion and a second portion, wherein the plurality of sensors is disposed in the first portion.

10. The air quality analysis device of claim 1, wherein the computing device comprises a user interface configured to display an instruction indicating that a user should clean a continuous positive airway pressure machine associated with the user.

11. A method of performing an air quality analysis, the method comprising:

receiving air quality data from an air quality analysis device, wherein the air quality analysis device comprises:

a housing having a chamber comprising an inlet port, wherein the inlet port is structured to receive an air flow into the chamber;

a plurality of sensors disposed within the chamber, wherein the plurality of sensors comprises at least one mold sensor, wherein the at least one mold sensor is configured to generate air quality data of a respiratory support apparatus based at least on a cleaning date associated with the respiratory support apparatus; and a printed circuit board in communication with the plurality of sensors and configured to transmit the air quality data to a computing device; and causing a user interface to display an instruction to a user associated with the respiratory support apparatus instructing the user to clean the respiratory support apparatus.

12. The method of claim 11, wherein the plurality of sensors further comprises at least one of a particulate matter sensor, a volatile organic compound sensor, a humidity sensor, or a temperature sensor.

13. The method of claim 12, wherein the particulate matter sensor is configured to generate air quality data indicating that there are particles having a diameter of less than 2.5 microns or 10 microns in the air flow.

14. The method of claim 11, wherein the plurality of sensors further comprises a first volatile organic compound sensor and a second volatile organic compound sensor, wherein the first volatile organic compound sensor is configured to generate air quality data indicating that there is a first volatile organic compound in the air flow and the second volatile organic compound sensor is configured to generate air quality data indicating that there is a second volatile organic compound in the air flow.

15. The method of claim 11, wherein the at least one mold sensor comprises a spectrometer.

16. The method of claim 11, wherein the chamber comprises an outlet port structured to discharge the air flow from the chamber.

17. The method of claim 16, wherein the inlet port is structured to receive the air flow into the chamber from a tube associated with the respiratory support apparatus and the outlet port is structured to discharge the air flow from the chamber into a face mask associated with the respiratory support apparatus.

18. The method of claim 16, wherein the inlet port is structured to receive the air flow into the chamber from a blower of the respiratory support apparatus and the outlet port is structured to discharge the air flow from the chamber into a tube associated with the respiratory support apparatus.

* * * * *